United States Patent [19]

Hirschberg

[11] Patent Number: 5,014,721
[45] Date of Patent: May 14, 1991

[54] BIPOLAR ELECTRODE LEAD FOR MEDICAL APPLICATIONS

[75] Inventor: Jakub Hirschberg, Taeby, Sweden

[73] Assignee: Siemens Aktiengesellschaft, Berlin & Munich, Fed. Rep. of Germany

[21] Appl. No.: 436,356

[22] Filed: Nov. 14, 1989

[30] Foreign Application Priority Data

Nov. 14, 1988 [EP] European Pat. Off. ............ 88118987

[51] Int. Cl.⁵ .............................................. A61N 1/05
[52] U.S. Cl. ..................................... 128/786; 128/785
[58] Field of Search ................................ 128/784–786, 128/419 P

[56] References Cited

U.S. PATENT DOCUMENTS

| | | | |
|---|---|---|---|
| 3,474,791 | 10/1969 | Bentov | 128/786 |
| 4,402,328 | 9/1983 | Doring | 128/786 X |
| 4,481,953 | 11/1984 | Gold et al. | 128/786 |
| 4,759,378 | 7/1988 | Swendson et al. | 128/786 |

FOREIGN PATENT DOCUMENTS 656313 6/1986 Switzerland ........................ 128/786
8502779 7/1985 World Int. Prop. O. .......... 128/786

*Primary Examiner*—Lee S. Cohen
*Attorney, Agent, or Firm*—Hill, Van Santen, Steadman & Simpson

[57] ABSTRACT

A bipolar electrode lead for medical applications, such as for electrical stimulation of body tissue, has an elongated conductor extending from a source of electrical stimulation to a tissue location to which the electrical stimulation is to be delivered. The conductor is surrounded by electrical insulation. The lead has an exposed electrode tip at the tissue location. The electrical conductor is in the form of a braided hose. The electrical insulation has a gap, which exposes the braided hose conductor, at a location spaced from the electrode tip. The exposed braided conductor functions as the neutral electrode.

3 Claims, 1 Drawing Sheet

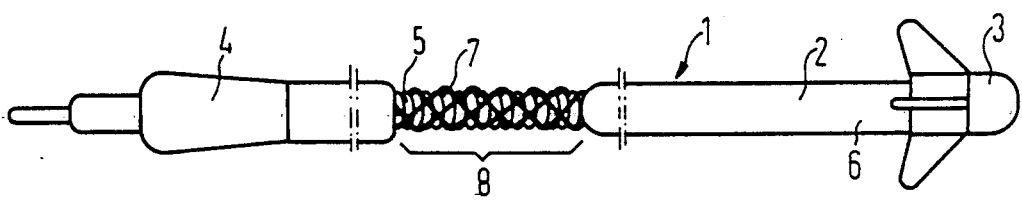

BIPOLAR ELECTRODE LEAD FOR MEDICAL APPLICATIONS

BACKGROUND OF THE INVENTION

1. Field of the Invention

The present invention is directed to a bipolar electrode lead for medical applications, particularly for use with an implantable heart pacemaker to deliver electrical stimulation pulses from circuitry within the pacemaker housing to a selected heart location.

2. Description of the Prior Art

The use of unipolar heart pacemaker electrode lead is known, wherein the pacemaker housing serves as the neutral electrode for the stimulation system. This requires that the return current path from the electrode at the lead tip travel through the intervening body tissue between the lead tip and the pacemaker housing. It is known that this can result in unwanted muscle stimulations and/or muscle inhibitions in the tissue surrounding the pacemaker housing.

A known solution to this problem is the use of a bipolar electrode lead, in which the neutral electrode is formed by an exposed ring of electrically conductive material disposed slightly spaced from the active electrode at the tip of the lead. If the tip of the lead is disposed, for example, inside the heart, the complete electrical current path will also be contained inside the heart. In order to keep the current density in the neutral electrode low, the ring must have a relatively large surface area.

The relatively large dimensions of the neutral electrode in such a bipolar arrangement result in considerable stiffening of the lead, which is otherwise extremely flexible. If, for example, the tip of the electrode lead is to be disposed in the left ventricle, the neutral electrode will also be in the left ventricle. Given the large number of bends to which the electrode lead is exposed, such a stiffening represents a high stress, which increases the risk that damage to the insulation, or a rupture of the conductor in the proximity of the stiffening, will occur.

If the bipolar lead is used as an atrial electrode, it can be bent into the shape of a J, so that the tip thereof can be applied in the right atrial appendage. Under such conditions, the neutral electrode cannot be disposed in the region of the bent portion of the lead, because of the aforementioned stiffening problem, and also because the neutral electrode is relatively heavy, compared to the remainder of the lead, so that an unwanted dislocation of the anchoring of the electrode tip can occur. If the neutral electrode is disposed at a greater distance from the distal end (i.e., the tip) of an atrial lead, it will come to lie in the vena cava in most cases. If the neutral electrode is disposed at that location, the current pulses associated with the neutral electrode can influence the phrenic nerve, which contains sensory fibers leading to parts of the pleura and diaphragm. Stimulation of the phrenic nerve can result in hiccups and coughing which are unpleasant for the patient.

A bipolar heart pacemaker electrode lead is described in U.S. Pat. No. 4,295,270 having an electrical conductor consisting of a braided hose which is connected to the neutral electrode. The neutral electrode is formed by a stiff ring, so that this electrode lead has the above-described disadvantages, despite the use of braided hose.

To make a bipolar electrode lead more elastic, a plurality of smaller neutral electrodes can be applied in succession along a portion of the lead. Such a lead is, however, relative complicated to manufacture, and is thus expensive.

SUMMARY OF THE INVENTION

It is an object of the present invention to provide a bipolar electrode lead suitable for use with an implantable heart pacemaker wherein the lead is elastic and flexible even in the region of the neutral electrode.

The above object is achieved in accordance with the principles of the present invention in an electrode lead wherein at least one of the electrically conductors is formed by a braided hose, and wherein a portion of the outer insulation is stripped away, thereby resulting in a gap in the insulation through which the braided hose conductor is exposed. The exposed portion of the braided conductor functions as the neutral electrode.

The neutral electrode can thus have an arbitrarily large surface area, while continuing to remain elastic and flexible, as the remainder of the electrode lead, without degrading the electrical properties of the electrode lead.

In a preferred embodiment of the invention, the conductor has an elongated core, with the braided hose proceeding over at least a portion of the core. This results in the braided hose contracting when a longitudinal pulling force acts on the electrode lead, so that the braided hose tightens around the core so that the core is not stretched or deformed in this region. This effect can be of particular advantage for an electrode lead wherein the core consists of a helical electrical conductor. A disadvantage of conventional leads using helical conductors is that the helix becomes elastically or plastically stretched in an undesirable manner when such longitudinal forces act thereon. This disadvantage is avoided in the present invention.

DESCRIPTION OF THE DRAWING

The single FIGURE is a side view of an electrode lead (schematically shortened) constructed in accordance with the principles of the present invention.

DESCRIPTION OF THE PREFERRED EMBODIMENTS

As shown in the drawing, a bipolar heart pacemaker electrode lead 1 constructed in accordance with the principles of the present invention consists of an electrode tip 3 at a distal end of the lead and an electrode connector 4 at a proximate end of the lead, with a lead section 2 therebetween. The connector 4 is adapted to be received in a known manner in a mating connector of a heart pacemaker housing (not shown). The lead section 2 consists of an elongated electrical conductor 5 with electrical insulation 6.

The electrode lead 1 has a further electrical conductor in the form of a braided hose 7. A section 8 of the braided hose 7 is not covered by electrical insulation 6, thereby forming a gap in the electrical insulation 6, so that the exposed portion 8 of the braided hose serves as the neutral electrode. This exposed portion is just as flexible as the remainder of the lead section 2.

As can also be seen in the drawing, the electrical conductor 5, which is surrounded by the exposed portion 8 of the braided hose 7, is helical, and is preferably insulated. The braided hose 7 can proceed over the entire length of the lead section 2 to the electrode tip 3. As a result, the helical conductor 5 is supported, so that it is not significantly deformed when a tensile force acts on the electrode lead 1.

In the exemplary embodiment shown in the drawing, the exposed portion 8 of the braided hose 7 is disposed at a sufficient distance from the electrode tip 3 to function as the neutral electrode for the electrical stimulation system. It will be understood by those skilled in the art, however that the exposed portion 8 can be arranged anywhere along the lead section 2 as may be useful for other purposes.

Although further modifications and changes may be suggested by those skilled in the art, it is the intention of the inventor to embody within the patent warranted hereon all changes and modifications as reasonably and properly come within the scope of his contribution to the art.

I claim as my invention:

1. A bipolar electrode lead for delivering electrical stimulation to a patient, said electrode lead comprising:

at least two elongated electrical conductors including an outer conductor formed by a braided hose, at least one of said conductors terminating in an active electrode adapted for exposure to body tissue of a patient to electrically stimulate said body tissue; and insulation surrounding said outer conductor having a gap therein exposing a portion of said braided hose to form a flexible non-stretchable neutral electrode for said active electrode.

2. A bipolar electrode lead as claimed in claim 1, wherein one of said electrical conductors forms an elongated core and wherein said conductor formed by a braided hose surrounds at least a portion of said elongated core.

3. A bipolar electrode lead as claimed in claim 2, wherein said elongated core is a helical electrical conductor.

* * * * *